(12) United States Patent
Gerlach et al.

(10) Patent No.: US 6,414,307 B1
(45) Date of Patent: Jul. 2, 2002

(54) METHOD AND APPARATUS FOR ENHANCING YIELD OF SECONDARY IONS

(75) Inventors: Robert L. Gerlach, Washington County; Locke Christman, Clackamas County; Mark Utlaut, Columbia County, all of OR (US)

(73) Assignee: FEI Company, Hillsboro, OR (US)

( * ) Notice: Subject to any disclaimer, the term of this patent is extended or adjusted under 35 U.S.C. 154(b) by 0 days.

(21) Appl. No.: 09/350,718

(22) Filed: Jul. 9, 1999

(51) Int. Cl.$^7$ ............................................. G01N 23/225
(52) U.S. Cl. ................... 250/309; 250/307; 250/492.21
(58) Field of Search ........................... 250/309, 492.21, 250/307; 438/789, 790

(56) References Cited

U.S. PATENT DOCUMENTS

| | | | |
|---|---|---|---|
| 5,113,072 A | 5/1992 | Yamaguchi et al. | 250/309 |
| 5,160,405 A | 11/1992 | Miyauchi et al. | 156/643 |
| 5,188,705 A | 2/1993 | Swanson et al. | 156/643 |
| 5,272,338 A * | 12/1993 | Winograd et al. | 250/309 |
| 5,376,791 A * | 12/1994 | Swanson et al. | 250/309 |
| 5,435,850 A | 7/1995 | Rasmussen | 118/726 |
| 5,495,110 A | 2/1996 | Ohnishi et al. | 250/309 |
| 5,798,529 A * | 8/1998 | Wagner | 250/309 |
| 5,827,786 A | 10/1998 | Puretz | 438/789 |
| 5,854,488 A | 12/1998 | Aita | 250/309 |
| 5,958,799 A | 9/1999 | Russell et al. | 438/712 |
| 6,281,496 B1 * | 8/2001 | Aita et al. | 250/309 |

FOREIGN PATENT DOCUMENTS

| | | |
|---|---|---|
| EP | 0 463 8780 A1 | 2/1992 |
| WO | WO 89/04052 | 5/1989 |

OTHER PUBLICATIONS

J.J. Hren, "Barriers to AEM: Contamination and Etching," *Introduction to Analytical Electron Microscopy*, Chap. 18, pp. 481–505, 1979.
A. Wagner et al., "Focused Ion Metrology" *J. Vac. Sci. Technol.*, vol. 13, Nov./Dec. 1995.
Shinji Matsui, "Cross–sectional observation of resist patterns by focused ion beam etching," Fundamental Research Laboratories, NEC Corporation, Aug. 6, 1993.
T.J. Stark et al., "$H_2o$ enhanced focused ion beam micromachining," *J. Vac. Sci. Technol.*, vol. 13 (6), pp. 2565–2569, Nov./Dec. 1995.
Shinji Matsui et al., "Electron beam induced selective etching and deposition technology," *J. Vac. Sci. Technol.*, vol. 7 (5), Sep./Oct. 1989.
T. Kosugi et al., "In situ patterning of GaAs by focused ion beam," *J. Vac. Sci. Technol.*, vol. 6, Nov./Dec. 1991.
B. Kempf et al., "$N_2/H_2O$: A New Gas Mixture for deep Groove ion Beam Etching of Long Wavelength Quaternary Mushroom Type Laser Structures," Japanese Journal of Applied Physics, Extended Abstracts, 22th Conf., Solid State Devices and Materials, 1990.
"Inspection, Measurement and Test," *Semiconductor International*, Mar. 1996.

* cited by examiner

*Primary Examiner*—Bruce Anderson
(74) *Attorney, Agent, or Firm*—Michael O. Scheinberg

(57) ABSTRACT

The sensitivity of a secondary ion mass spectrometer (SIMS) is increased by using water vapor to enhance the yield of positive secondary ions sputtered by a primary focused ion beam. Water vapor is injected through a needle that is positioned close to the sample and electrically biased to reduce interference with secondary ion collection field. The sensitivity is enhanced for metals in particular, which tend to be sputtered as positive ions.

21 Claims, 8 Drawing Sheets

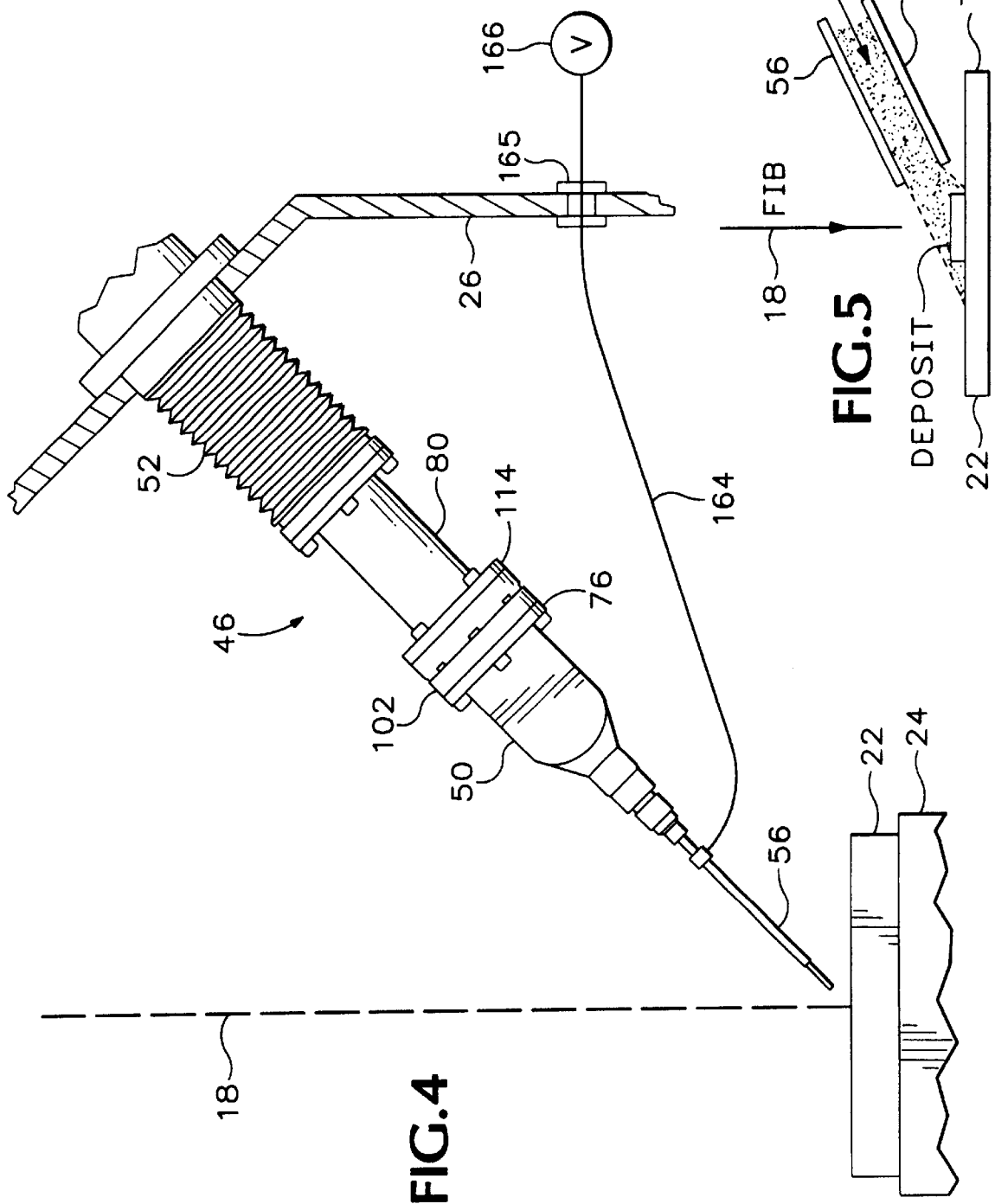

METHOD AND APPARATUS FOR ENHANCING YIELD OF SECONDARY IONS

TECHNICAL FIELD

The present invention relates to the field of materials characterization, and in particular, to enhancing the yield of secondary ions for mass spectrometric analysis.

BACKGROUND OF THE INVENTION

Focused ion beam (FIB) systems are widely used in semiconductor manufacturing because of their ability to image, etch, deposit, and analyze with extremely fine resolution. Secondary Ion Mass Spectrometry (SIMS) is a method, often used in conjunction with FIB systems, for determining the composition of a sample. In the SIMS process, the ion beam is used to sputter, that is, physically eject by energy transfer, particles such as atoms, molecules, and clusters, from the sample. A small percentage of these ejected particles are ionized, that is, they gain or lose one or more electrons during the sputtering process and are thereby electrically charged. Such ejected charged particles are known as secondary ions, as opposed to the primary ions in the focused ion beam. By passing the secondary ions through a mass spectrometer that includes a combination of magnetic and/or electric fields, it is possible to determine the charge-to-mass ratio of the secondary ions and then to deduce their composition.

Ideally, an analyst can detect the presence of a very small amount of a substance and pinpoint exactly where on a specimen the substance was located. The sensitivity of a SIMS is a measure of its ability to detect small quantities of a substance. Because the features size in modern integrated circuits is often as small as 0.12 micron, a very small contaminant can ruin a circuit. Thus, being able to characterize precisely a small amount of contaminant at a precise location is critical to determine the causes of circuit defects and to characterize circuit fabrication processes.

The ability of a SIMS to detect the presence of a material depends on the type of material being analyzed, the concentration of that material in the area being sputtered, the total amount of material sputtered from the sample, and the probability that the material sought will be ejected as a detectable ion and not as an undetectable neutral particle. Unfortunately, most of the particles sputtered from a specimen are not ionized and cannot be analyzed in the mass spectrometer, which uses electric and/or magnetic fields to separate charged particles.

The probability of a particle being ejected as an ion depends upon the elemental composition of the particle, the chemical environment around the particle on the sample, and the type of ions in the primary ion beam. Primary beams of oxygen or cesium ions are used for SIMS analysis with satisfactory secondary ion yields. Such beams, however, typically have a spot size of greater than one micron and cannot provide the extremely fine resolution of liquid metal source ion beams. Gallium liquid metal ion source (LMIS) primary ion columns, for example, can provide 5 nm to 7 nm lateral resolution on commercially available FIB systems. Because of their ability to image, sputter, and deposit with such great precision, FIB systems have gained nearly universal acceptance as a necessary analytical tool for semiconductor design, process development, failure analysis, and most recently, defect characterization. In support of these applications, the addition of a SIMS to the FIB has expanded the applications of the tool to include elemental analysis having sub-micron spatial resolution.

The smaller spot size of the gallium beam necessitates fewer ions in the beam, that is, reduced beam current, so the total number of ejected particles available for detection is correspondingly reduced. Moreover, the secondary ion yield, that is, the number of secondary ions ejected for each primary ion, from a gallium source can be a factor of 100 less than that of an oxygen primary beam. Thus, although the smaller gallium beam provides much greater precision in determining the position from which a particle is ejected, the total number of ions ejected is reduced and the probability of the particles that are ejected being ionized and detected is greatly reduced. Thus, SIMS used with LMIS is not as effective as analysts desire.

The yield of secondary ions also depends on the chemistry of the specimen. It is known that if a surface is oxidized the percentage of positive ions produced during the sputtering process increases compared to the number for an unoxidized surface. Most metals and semiconductors are more likely to lose an electron than to gain one and are therefore more likely to become positive ions than negative ones. Thus, the SIMS sensitivity for metals and semiconductors from an oxidized surface is increased. It has therefore become common practice to introduce oxygen as a gas into the vacuum system in order to oxidize the surface. It is also known to use an oxygen ion primary beam, with or without oxygen gas introduction, to enhance secondary ion yield. Using an oxygen ion beam, however, is not possible in the majority of modern FIB systems, which are designed to use a LMIS and, as described above, oxygen primary ion beams lack the spatial resolution to be useful in many applications.

SUMMARY OF THE INVENTION

Thus, it is an object of the invention to increase the sensitivity of SIMS systems.

It is another object of the invention to increase the sensitivity of SIMS systems used with a sub-micron spot size LMIS FIB system.

It is a further object of the invention to facilitate elemental analysis of sub-micron features using SIMS.

It is yet another object of the invention to enhance detection of metallic and semiconductor materials using SIMS.

It is still another object of the invention to increase the secondary ion yield using a safe, non-toxic agent.

It is yet a further object of the invention to introduce an agent onto the target surface while minimizing the reduction in secondary ion collection efficiency reduction caused by the agent introduction apparatus.

It is still a further object of the invention to minimize the disruption of the secondary ion extraction field caused by the agent introduction apparatus.

It is yet a further object of the present invention to improve the sensitivity of SIMS in existing LMIS FIB without requiring expensive system modifications.

In accordance with the invention, water is introduced onto the surface of the specimen in an area that is being sputtered for SIMS. The introduction of water has been found to result in a significant enhancement of the secondary ion yield for most materials, including silicon, aluminum, titanium, molybdenum, and tungsten.

The water is introduced preferably using a gas nozzle near the target point of the primary beam, so that the water molecules have a high probability of sticking to the surface from which particles are sputtered. To prevent the close proximity of the nozzle to the surface from adversely affecting the secondary ion extraction field and degrading the collection efficiency, the nozzle may be electrically biased.

The present invention provides improved SIMS sensitivity on existing LMIS FIB systems that are in common use in the semiconductor and other industries. Enhancement of secondary ion yields significantly improves detection sensitivity and thereby facilitates elemental analysis of smaller (sub-100 nm) features.

Additional objects, advantages and novel features of the invention will become apparent from the detailed description and drawings of the invention.

BRIEF DESCRIPTION OF THE DRAWINGS

FIG. 4 is a partial, enlarged side view, broken away, of the gas injection system of FIG. 1;

FIG. 5 is a further enlarged schematic side view of the gas injection nozzle of FIG. 4;

DETAILED DESCRIPTION OF PREFERRED EMBODIMENTS

The system according to a preferred embodiment of the present invention includes a charged particle beam system that includes a gas injection system for injecting water vapor towards the area of the specimen surface impacted by the beam and a secondary ion mass spectrometer for analyzing particles ejected from a specimen.

Figure 1:
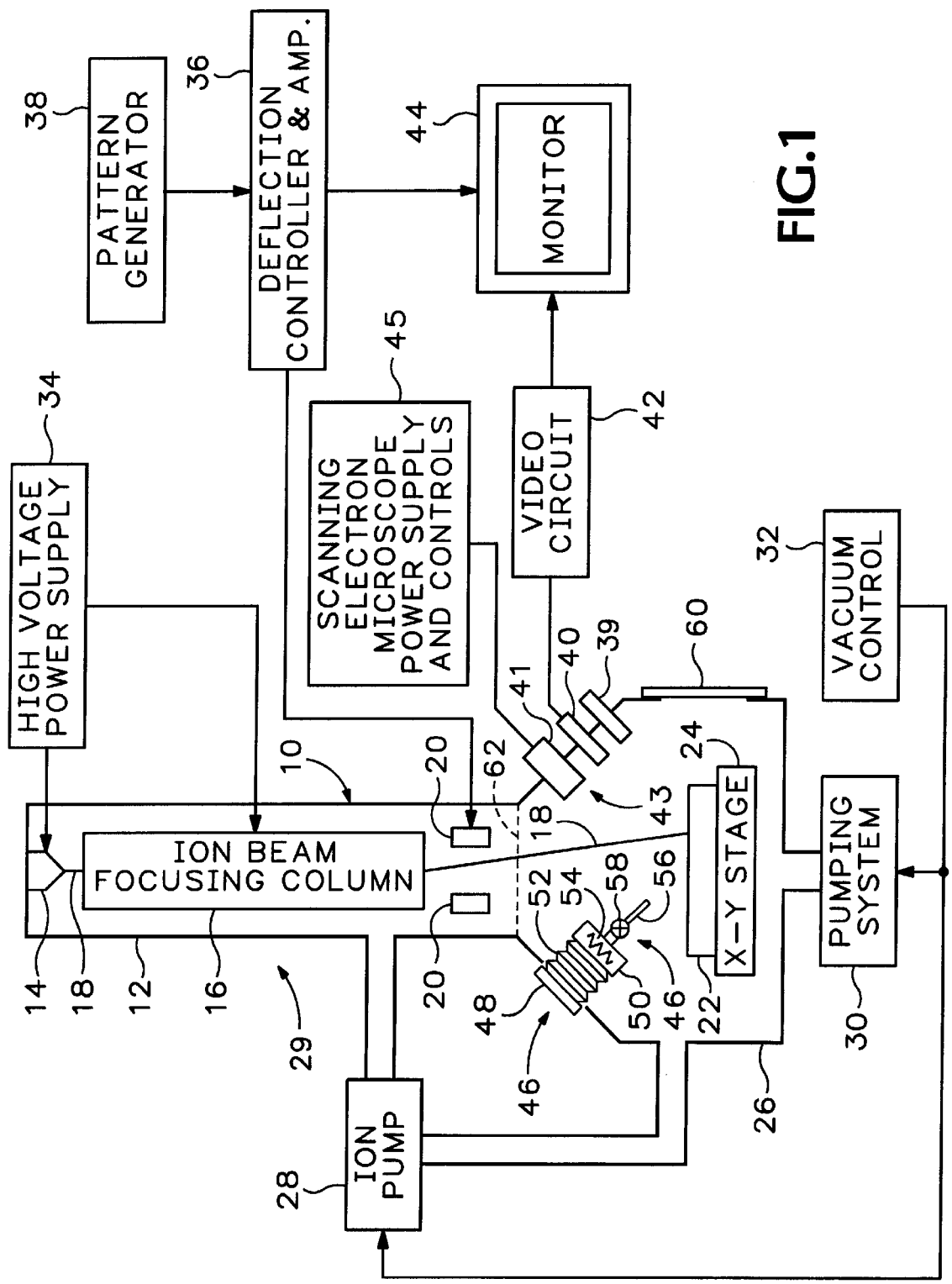
FIG. 1 is schematic representation of a focused ion beam system used to sputter ions for analysis in accordance with the present invention.

Referring to FIG. 1, which schematically illustrates a focused ion beam system for carrying out the present invention, an evacuated envelope 10 includes an upper neck portion 12 within which are located a liquid metal ion source 14 and a focusing column 16 which includes extractor electrode means and an electrostatic optical system. An ion beam 18 passes from source 14 through column 16 and between electrostatic deflection means schematically indicated at 20 toward a sample 22, which typically comprises a semiconductor device positioned on a movable X-Y stage 24 within a lower chamber 26. Components for generating, focusing, and directing the ion beam are referred to collectively as an ion beam generator 29. An ion pump 28 is employed for evacuating neck portion 12. The chamber 26 is evacuated with turbomolecular and mechanical pumping system 30 under the control of vacuum controller 32.

High voltage power supply 34 is connected to liquid metal ion source 14 as well as to appropriate electrodes in focusing column 16 for forming an approximately 30 keV ion beam 18 and directing the same downwardly. Deflection controller and amplifier 36, operated in accordance with a prescribed pattern such as a raster pattern provided by pattern generator 38, is coupled to deflection plates 20 whereby beam 18 may be controlled to trace out a corresponding pattern on the upper surface of sample 22.

Figure 2:
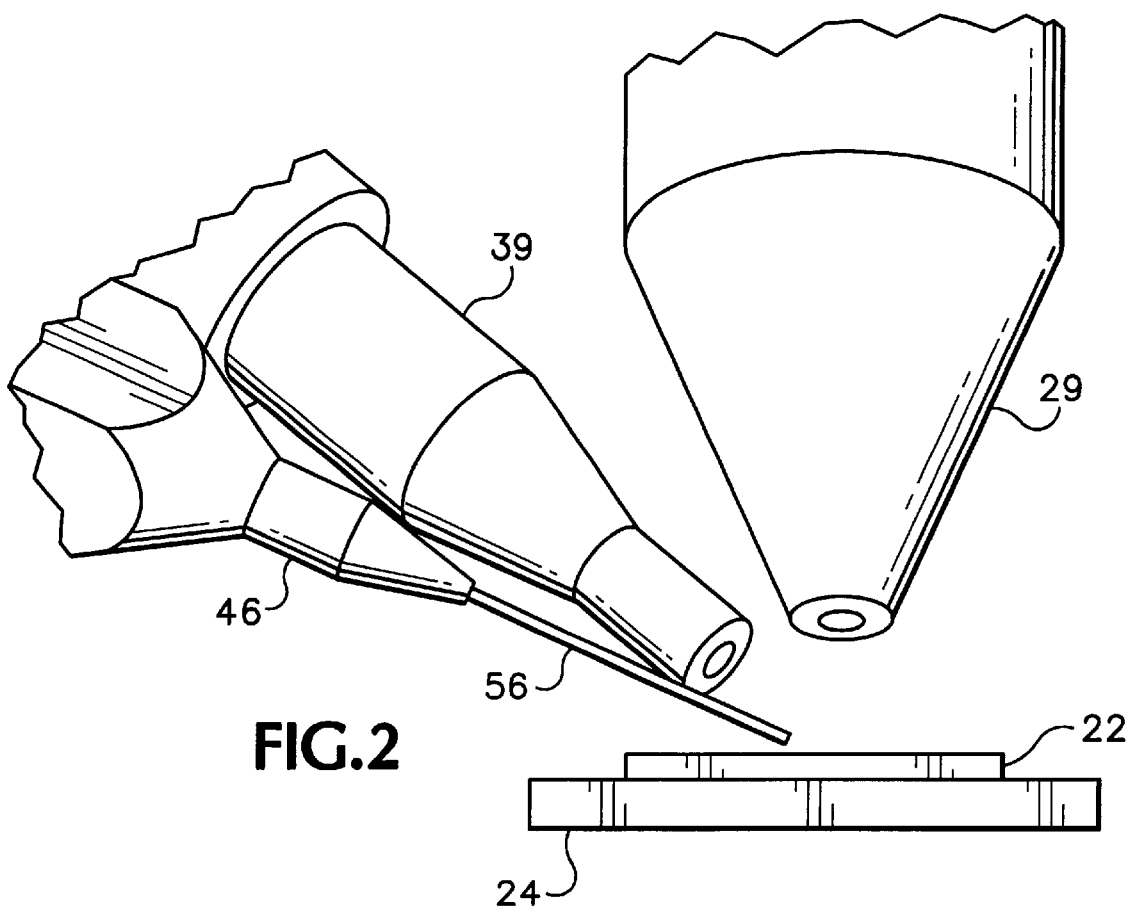
FIG. 2 is a enlarged partial view showing the relative positions near the sample of components of the focused ion beam system of FIG. 1.

The source 14 typically provides a metal ion beam of gallium, although other metallic ions such as indium or aluminum can be used. The invention can also be used with beams of non-metallic ions, such as oxygen and cesium. The liquid metal ion source is capable of being focused into a sub 0.1 micron width beam at sample 22 for either modifying the surface 22 by etching away or depositing material, for imaging the surface 22, or for analyzing materials present in sample 22 using a secondary ion mass spectrometer 39, described in detail below. A gas injection system, gas source 46, provides for injecting gases for interacting with sample 22 and ion beam 18. FIG. 2 is an enlarged view of portions of ion beam generator 29, gas source 46, and SIMS 39, showing their relative positions near sample 22.

An electron multiplier 40 used for detecting secondary emission for imaging is connected to video circuit and amplifier 42, the latter supplying drive for video monitor 44 also receiving deflection signals from controller 36. Evacuated envelope 10 may optionally include a scanning electron microscope (SEM) 43 that can be used to view the results of operations performed by the focused ion beam or that can perform electron beam processing. SEM 43 includes an electron beam generator 41 and associated power supply and controls 45. A preferred focused ion beam system that includes an SEM is the DualBeam™ XL860 model from FEI. Company, the assignee of the present invention.

Figure 3:
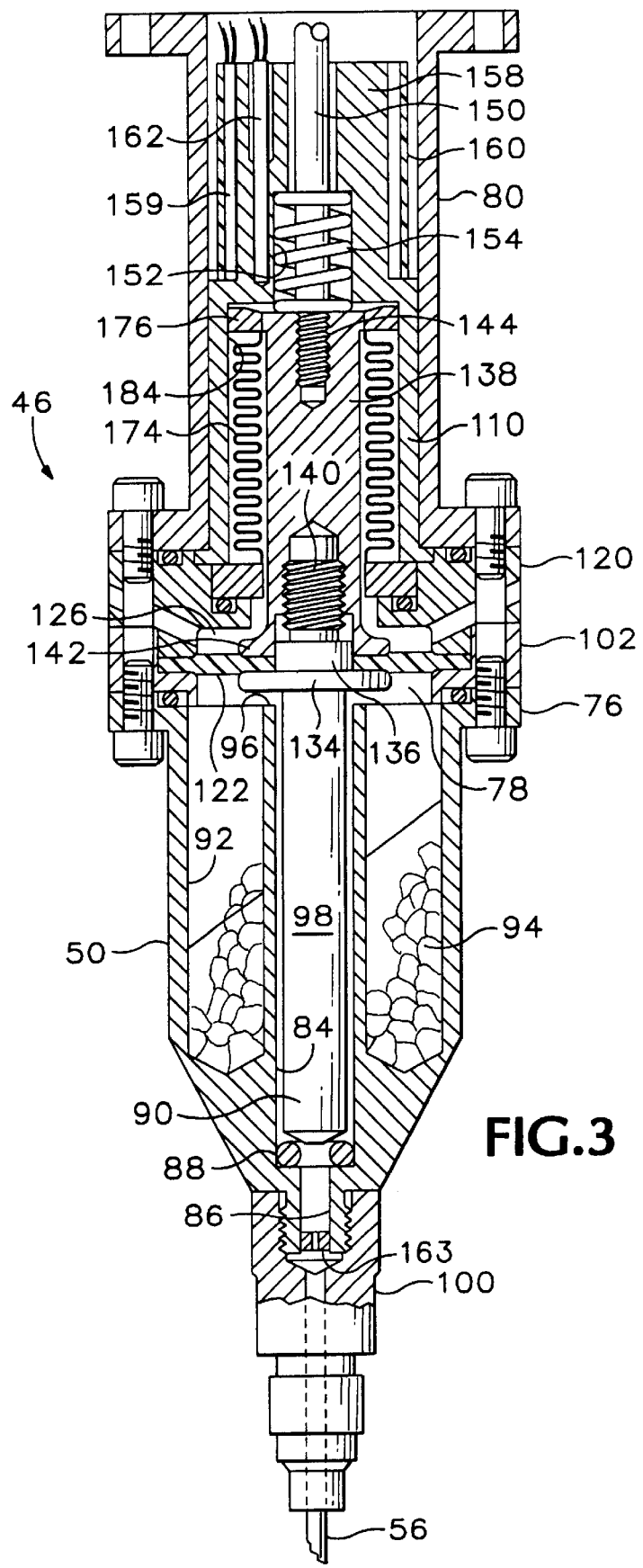
FIG. 3 is a partial cross-sectional view of a gas containment apparatus employed for injecting water vapor towards a substrate inside the FIB system of FIG. 1.

A preferred gas source 46 is located inwardly of the side of chamber 26 by translation device 48 adapted for positioning said source via support means within bellows 52. U.S. Pat. No. 5,435,850 to Rasmussen for a "Gas Injection System" assigned to the assignee of the present invention discloses an apparatus for introducing and directing gaseous vapor toward-sample 22. Referring to FIG. 3, gas source 46 comprises a reservoir 50 within which a water vapor source 94 is received. Water vapor source 94 typically comprises granules of a hygroscopic salt, such as magnesium sulfate, that will release water vapor without introducing other contaminants into evacuated envelope 10. The lower end of reservoir 50 is provided with nozzle in the form of needle 56 comprising a capillary tube having a small orifice for directing gas toward substrate 22. Needle 56 has an internal diameter of approximately 0.5 mm and is typically positioned about 100 $\mu$m from the sample 22. Needle 56 is attached to the threaded lower end of reservoir 50 by lock fitting 100. To isolate electrically needle 56, lock fitting 100 is made from an electrically insulating material, such as Delrin® and needle 56 is not in contact with an metal parts of gas source 46.

Upper flange 76 of reservoir 50 is secured to the periphery of sealing chamber 78, the latter depending ultimately from support tube 80. Support tube 80 is attached with screws to the lower end of bellows 52 as well as to positioning mechanism (not shown) within the bellows. Reservoir 50 comprises a solid metal block elongated in a direction longitudinal of needle 56 and provided with a central cylindrical passage 84 through which gas passes to the hypodermic needle. At its lower end, the longitudinal passage 84 narrows at 86, forming a shoulder for receiving O-ring valve seal 88 that cooperates with the tapered end of valve plunger 90 for regulating the flow of gas from passage 84 to needle 56. Plunger 90 is located at the lower end of actuator 98, the latter comprising a rod disposed coaxially within passage 84 and extending back through the passage. The outer diameter of actuator 98 is less than the inside diameter of passage 84 in order to form a channel for the delivery of gas.

Around central passage 84 in reservoir 50 are disposed a plurality of elongated cylindrical chambers 92 parallel to and in substantially surrounding relation with cylindrical passage 84, each chamber 92 comprising a longitudinal bore in the reservoir block 50 adapted to receive water vapor source material 94. The upper end 96 of the reservoir is open to sealing chamber 78 wherein water vapor generated within the reservoir chamber is communicated to central passage 84.

Center rod extension 138 is threadably engaged at 140 by the end of actuator 98 whereby the center of membrane 122 is sealingly disposed between flange 134 and head 142 of center rod extension 138. Metal bellows 174 separates region 126 above membrane 122 from atmospheric pressure within support tube 80. The bellows 174 extends between rings 170 and 176, the former being locked between spacer ring member 120 and heat sink 110, while the latter is secured to the upper end of center rod extension 138 proximate the end of cavity 184 of sink 110 within which it slides as rod 150 is moved against the bias of spring 154 to open and close the valve comprising plunger 90 and O-ring 88.

Membrane 122 defines the upper wall of sealing chamber 78 and a lower wall of region 126 which is vented to chamber 26. Actuator 98 includes a radial flange 134 within chamber 78 for centrally engaging the membrane 122 which is peripherally held, while portion 136 of the actuator passes through a central aperture in membrane 122 and into a recess within the head end of center rod extension 138. Actuator 98 has a threaded portion 140 adapted to engage a mating thread in center rod extension 138.

The center rod extension 138 is provided with an upper internal threaded portion 144 mating with threads 14 at the lower end of actuating rod 150. Rod 150 is adapted to receive linear motion under the control of means within the positioning mechanism inside bellows 52 in FIG. 1 or there beyond. Upper cavity 152 in heat sink 110 houses spring 154 acting between the heat sink and the upper end of center rod extension 138 so that the center rod extension and attached parts including actuator 98 are normally biased in a direction for closing plunger 90 against O-ring 88 to close off the flow of gas. However, when rod 150 is pulled upwardly (by means not shown) the valve is opened as center rod extension 138 and ring 176 slide within lower recess 184 in heat sink 110. The membrane 122 flexes with movement of the actuator.

Upper end portion 158 of heat sink 110 is of reduced cylindrical diameter and receives there around a band heater 159 provided electrical current by means not shown, the heater being covered and held in place by shrink band 160. A thermistor 162 is embedded within portion 158 of the heat sink, and when electrical current is supplied to band heater 159, the thermistor 162 provides feedback to a control circuit for regulating the temperature of the heat sink at a desired elevated level for heating the reservoir 50 and the material there within. The heater and control therefor are conveniently located outside the vacuum region of chamber 26 eliminating electrical feedthroughs, but the heat generated is conducted via the vacuum wall to the reservoir.

The gas injection system 46 forms a housing providing an enclosure for generating and containing gas there within, the enclosure including chambers 92 and central passage 84 of reservoir 50 as well as sealing chamber 78 surrounded by the lower end of sealing member 102. The gas tight enclosure additionally comprises the flexible rubber membrane 122 clamped between sealing member 102 and spacer ring member 120 at the periphery thereof, while also being centrally clamped in sealing relation to actuator 98 between actuator flange 134 and the head 142 of center rod extension 138 as previously mentioned.

When reservoir 50 is at a desired temperature for sublimating water from the hygroscopic compound within reservoir 50, valve 58 may be opened by withdrawing actuator rod 150 (FIG. 3) from outside the apparatus to open and regulate the position of valve plunger 40, while the nozzle 56 is directed towards the desired area of the sample as shown enlarged in FIG. 4 and further enlarged in FIG. 5. An aperture 163 positioned between passage 84 and needle 56 restricts the flow of water vapor. Applicants have found that a suitable flow of water vapor is maintained if water vapor is sublimated from magnesium sulfate granules at room temperature and aperture 163 has a diameter of approximately 25 $\mu$m. The water vapor will then cause the background pressure in the chamber to reach approximately $5\times10^{-5}$ mBar.

FIG. 4 also shows a conductor 164 attached to needle 56 to provide a biasing voltage as described below. Conductor 164 extends through the wall of low chamber 26 by way of a seal 165 to an adjustable voltage source 166. Bellows 52 accommodates movement of the needle assembly and reservoir relative to the sample without affecting the vacuum within chamber 26. To establish a given gaseous flux, the reservoir is heated to a predetermined temperature. Operating temperature range will vary depending upon the hygroscopic material and its moisture content and heating may not be required above room temperature.

Another type of water vapor delivery system is described in T. J. Stark at al., "H$_2$O Enhanced Focused Ion Beam Micromachining" J. Vacuum Science and Technology B, 13(6), pp. 2565–69 (Nov./Dec. 1995). In this system, water vapor flows from a reservoir outside the chamber 26 and is controlled by a needle valve. The gas pressure at the entrance to needle 56 can be monitored using a Granville-Philips convection gauge. The needle valve is adjusted to maintain a suitable background pressure in the chamber, approximately $5\times10^{-5}$ mBar in one implementation.

Another type of gas delivery system is described in U.S. Pat. No. 5,149,974 to Kirch et al. for "Gas Delivery For Ion Beam Deposition and Etching." This gas delivery system introduces a gas into a cylinder positioned above the specimen and coaxial with the ion beam. The cylinder has apertures for the ion beam to enter and exit, and the gas migrates to the specimen surface through the bottom aperture. The cylinder may also include a deflection means for applying an electric or magnetic field to deflect secondary particles out of the cylinder for detection.

A door 60 is opened for inserting sample 22 on stage 24 which may be heated, and also for servicing the reservoir 50. The door is interlocked so that it cannot be opened if the temperature in reservoir 50 is substantially above room temperature. A gate valve, schematically illustrated at 62, is closed before door 60 can be opened to seal off the ion source and focusing column apparatus. The vacuum control system along with the heater of gaseous vapor source 46 are operated to provide an appropriate vapor pressure condition for establishing a gaseous vapor flux in chamber as directed toward substrate 22 for sputtering sample 22.

The high voltage power supply provides an appropriate acceleration voltage to electrodes in ion beam column 16 for energizing and focusing ion beam 18. When it strikes the sample having condensed water vapor adhered thereupon, the ion beam provides energy for initiating a reaction between the water vapor and sample 22 and for sputter etching sample 22.

Deflection controller and amplifier 36 causes the ion beam to be deflected in a desired pattern but wherein deflection of the ion beam is at a rate slow enough for etching sample 22. Considerations regarding deflection speed, loop time, etc. are well understood by those skilled in the art.

As hereinbefore mentioned, the vacuum system provides a vacuum of between approximately $1 \times 10^{-6}$ Torr and $5 \times 10^{-4}$ Torr within chamber 26. With emission of gaseous vapor, the chamber background pressure is suitably about $10^{-5}$ Torr. In an exemplary embodiment, the gaseous source 46 is heated to a temperature for providing a gaseous flux of roughly $1 \times 10^{16}$ to $1 \times 10^{17}$ molecules per second per square centimeter via the capillary tube of needle 56, while the metal ion source and focusing column are suitably controlled for generating a flux of $1 \times 10^{13}$ to $1 \times 10^{15}$ charged particles per second per square centimeter within the rastered area. A pressure of approximately 0.1 Torr is obtained near the sample surface while the pressure of the chamber remains below about $8 \times 10^{-5}$ Torr. The exact water pressure at the specimen is not critical, and the pressures and flow parameters can be easily determined for any particular implementation by increasing the water vapor flow until the secondary ion count increases to the desired level. The amount of water vapor in the system should be sufficient to enhance the secondary ion yield without degrading the background vacuum to unacceptable levels. Skilled persons can readily determine appropriate pressures and gas flows for any particular application.

In operation, the system according to the present invention is advantageously employed to carry out secondary ion mass spectrometry or SIMS whereby the sample bombarded by focused primary ion beam 18 is analyzed for elemental content. SIMS are available as accessories on most focused ion beam systems, including those available from FEI Company, the assignee of the present application. SIMS are also available separately from, for example, ABB Extrel, Pittsburgh, Pa. Sample 22 is placed on stage 24 while the moisture bearing magnesium sulfate granules are deposited in crucible 50, after which the chamber 26 is closed and evacuated and gate 62 is opened so that an ion beam 18 can be generated and directed toward the sample. The sample can be positioned by movement of stage 24 in a well understood manner. Needle 56 is positioned so that water vapor can be directed towards the area of interest. Depending upon the water vapor source material used, sufficient water vapor may evolve from the material at room temperature or crucible 50 may be heated by element 54 to produce water vapor. As water vapor is produced, valve 58 is opened to permit escape of the water vapor. Pattern generator 38 can be programmed to deflect ion beam 18 in a raster pattern corresponding to a specific area of sample 22 in a well understood manner on monitor 44.

To provide sufficient water molecules adhered to the surface of sample 22 while maintaining a sufficient vacuum in section 26 for the focused ion beam to function, needle 56 is positioned very near specimen 22, preferably within 100 $\mu$m. Positioning metal needle 56 so near specimen 22, unfortunately, interferes with the electric field used to collect secondary ions, resulting in a reduced collection efficiency. By using conductor 164 (FIG. 4) to electrically bias needle 56, the interference with the collection field can be significantly reduced. The preferred biasing voltage used varies with the position of needle 56 and with the configuration of the secondary ion collection optics. The proper bias voltage can be readily determined by varying the bias voltage until the secondary ion count is maximized.

As the water vapor is directed toward sample 22, water is adsorbed on the sample surface. As the focused ion beam scans a surface of a sample, energy is provided for enabling a chemical reaction to take place between water and the material of said surface, and the reaction product is removed or sputtered away.

Figure 6:
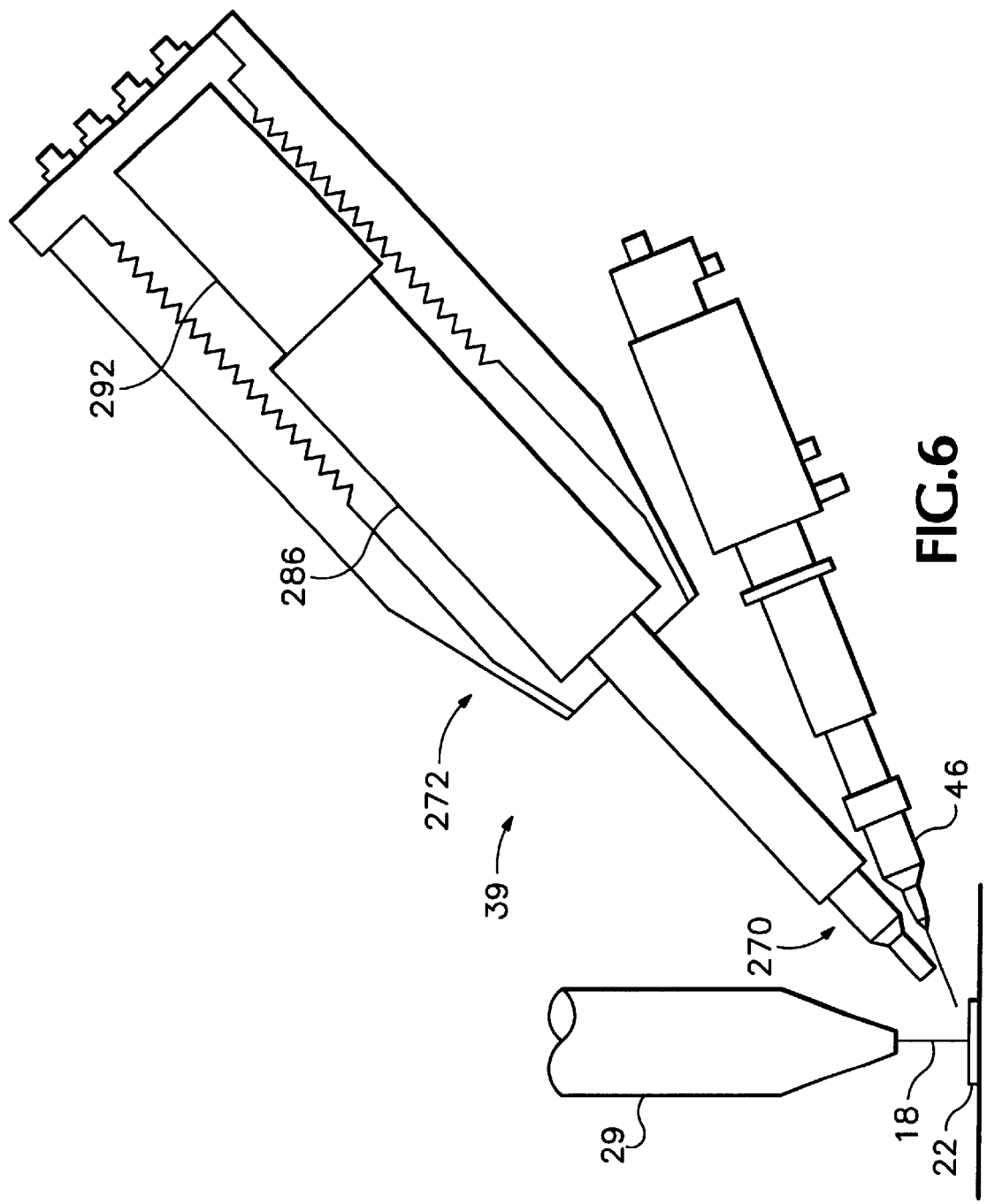
FIG. 6 a schematic representation of a quadrupole mass spectrometer used with the focused ion beam of FIG. 1.

Referring to FIG. 6, illustrating in schematic form an apparatus according to the present invention, extraction and transport optics 270 are positioned with respect to the ion beam column for collecting secondary ions produced at sample 22 by virtue of impingement of the primary ion beam 18. The transport optics direct secondary ions toward a quadrupole mass spectrometer 272.

The collected secondary ions directed to mass spectrometer 272 are first passed through lenses (not shown) for focusing the ion stream so that it can be analyzed. The focused ion stream then passes through mass spectrometer 272 and to an ion detector 292. Ion detector 292 converts the ions into signals appropriate for coupling to an electronic system including a computer for calculating and collecting analysis results. The ion detector 292 suitably comprises an electron multiplier receiving ions from the mass spectrometer and electrons consequently produced in the electron multiplier provide an appropriate output signal. The detailed construction and operation of the quadrupole mass spectrometer and ion detector is well known and understood by those skilled in the art.

In accordance with the present invention, the quantity of secondary ions produced for analysis is greatly increased by virtue of the introduction of water vapor from source 46, thereby enhancing the sensitivity and accuracy of analysis while using a LMIS that provides lateral resolution of less than 10 nm. It is postulated that the dramatically increased-production-of ions is a result of increased sticking of $H_2O$ compared to $O_2$ and an enhanced conversion of neutral to ionic sputtered species. No plumbing of an external gas is required, and the same system can be used for analysis as well as for machining a sample. Machining can be advantageously employed in conjunction with analysis when the chemistry of a particular buried layer is to be investigated, since the ion beam can be first used to machine down to the desired layer.

Figure 7:
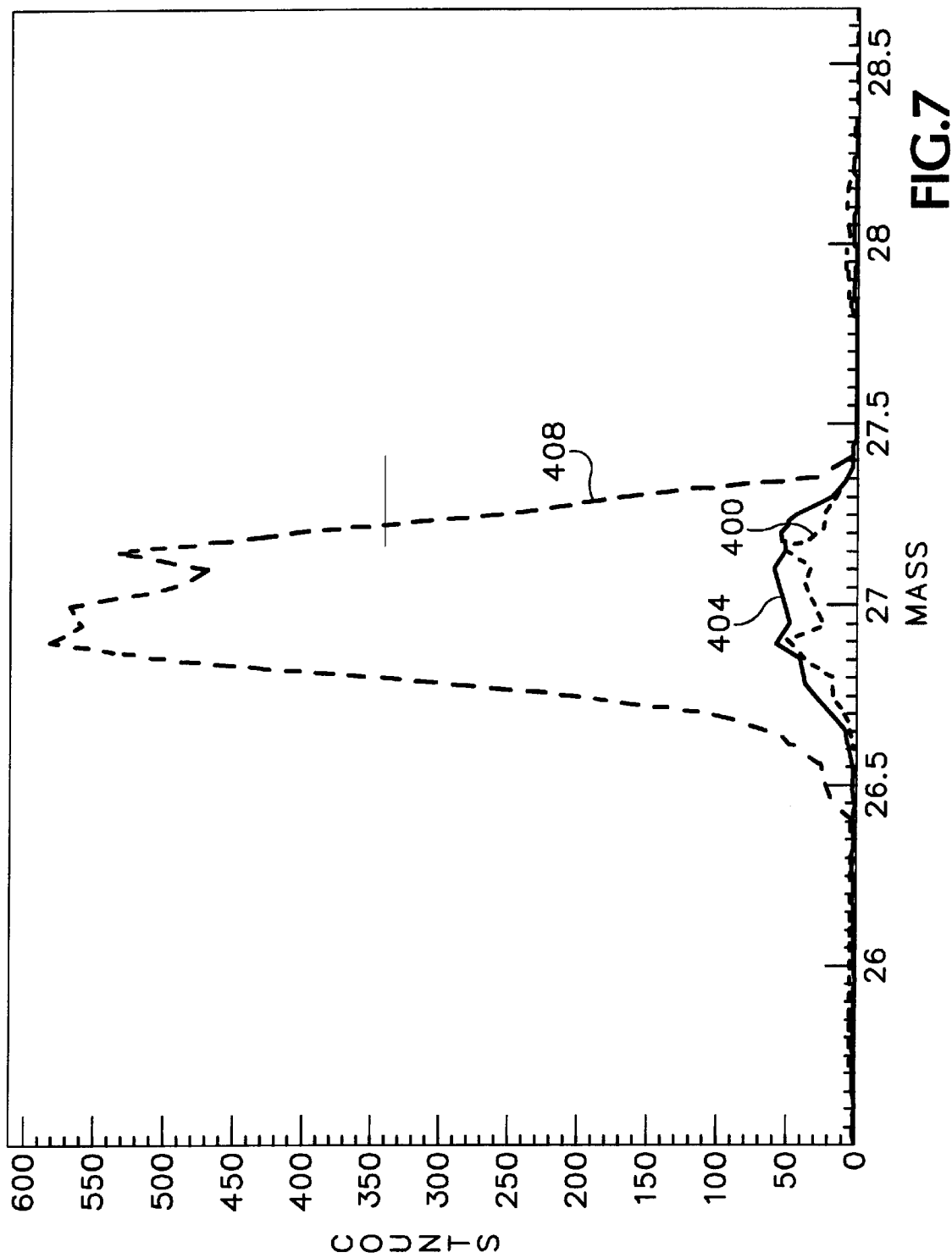
FIG. 7 shows a graph of the number of secondary ions detected from an aluminum sample with and without using the present invention.

FIG. 7 shows the number of positive ions of different masses detected within a fixed time period from an aluminum sample sputtered under three different conditions by a focused ion beam. Line 400 shows the number of ions of various masses detected with no water vapor injection and with the gas injection needle 56 removed from the vicinity of the sample. Line 404 shows the number of ions of different masses detected with no water vapor injection, but with the gas injection needle 56 positioned near the sample and electrically biased. The background vacuum pressure during ion counting for lines 400 and 404 was about $5.5 \times 10^{-7}$ mbar. Line 408 shows the number of ions of different masses detected with water vapor injection and with a bias voltage applied to the injection needle 56. The background vacuum pressure with water vapor injection present was about $3.3 \times 10^{-5}$ mbar. The total number of ions counted in the fixed time period with water vapor injection was 566, whereas the total number of ions counted without water vapor injection was 54 with the needle in and biased and 34 with the needle removed.

Figure 8:
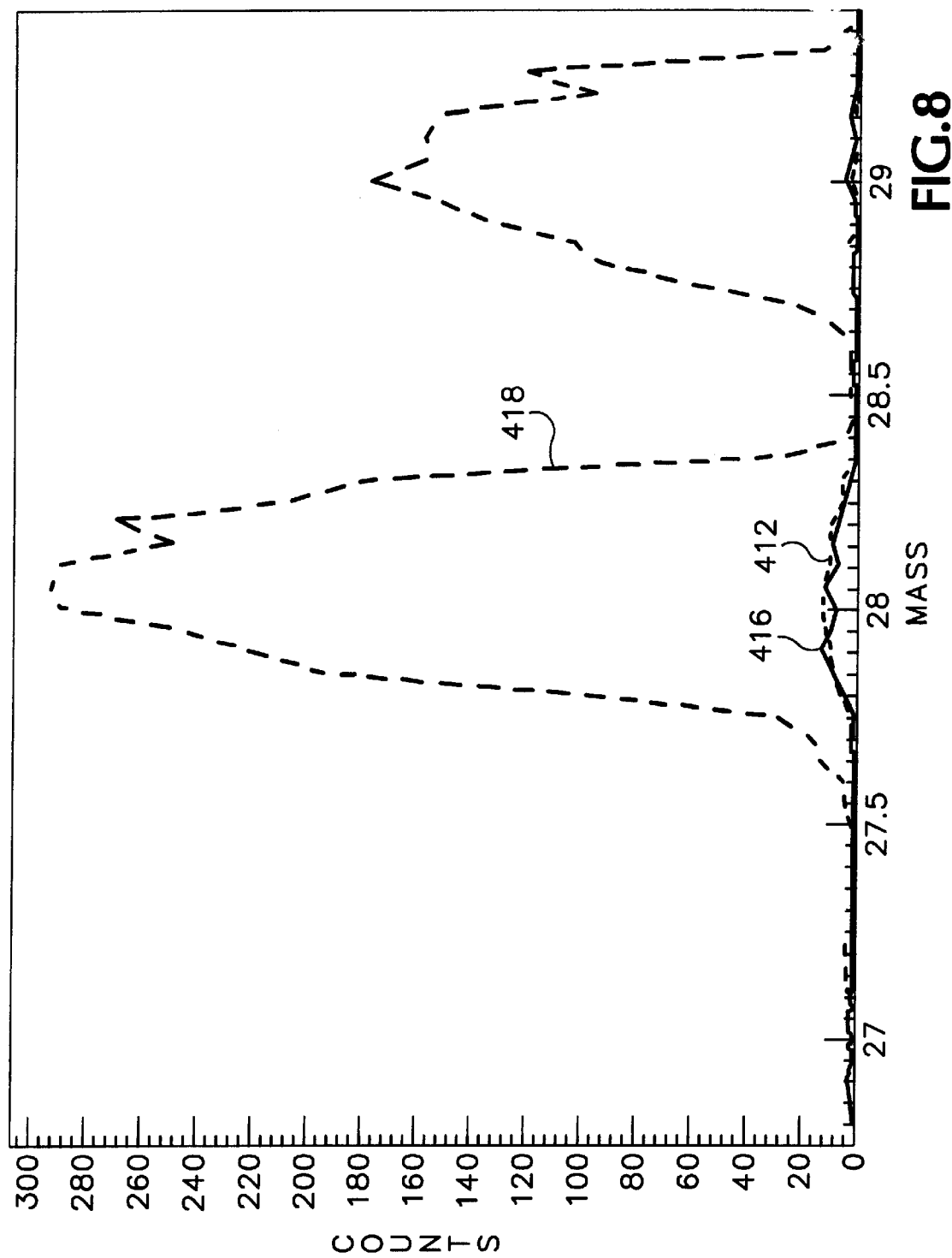
FIG. 8 shows a graph of the number of secondary ions detected from an silicon sample with and without using the present invention.

FIG. 8 is similar to FIG. 7, but the sample comprises primarily silicon. Line 412 shows the number of ions of different masses detected with no water vapor injection and with the gas injection needle 56 removed from the vicinity of the sample. Line 416 shows the number of ions of different masses detected with no water vapor injection, but with gas injection needle 56 near the sample and electrically biased. The background vacuum pressure during ion counting for lines 412 and 416 was about $5.5 \times 10^{-7}$ mbar. Line 418 shows the number of ions of different masses detected with water vapor injection and with a bias voltage applied to the injection needle 56. The background vacuum pressure with water vapor injection present was about $3.3 \times 10^{-5}$ mbar. The total number of ions counted in the fixed time period with water vapor injection was 291, whereas the total number of ions counted without water vapor injection was 8 with the needle in and biased and 11 with the needle removed.

Figure 9:
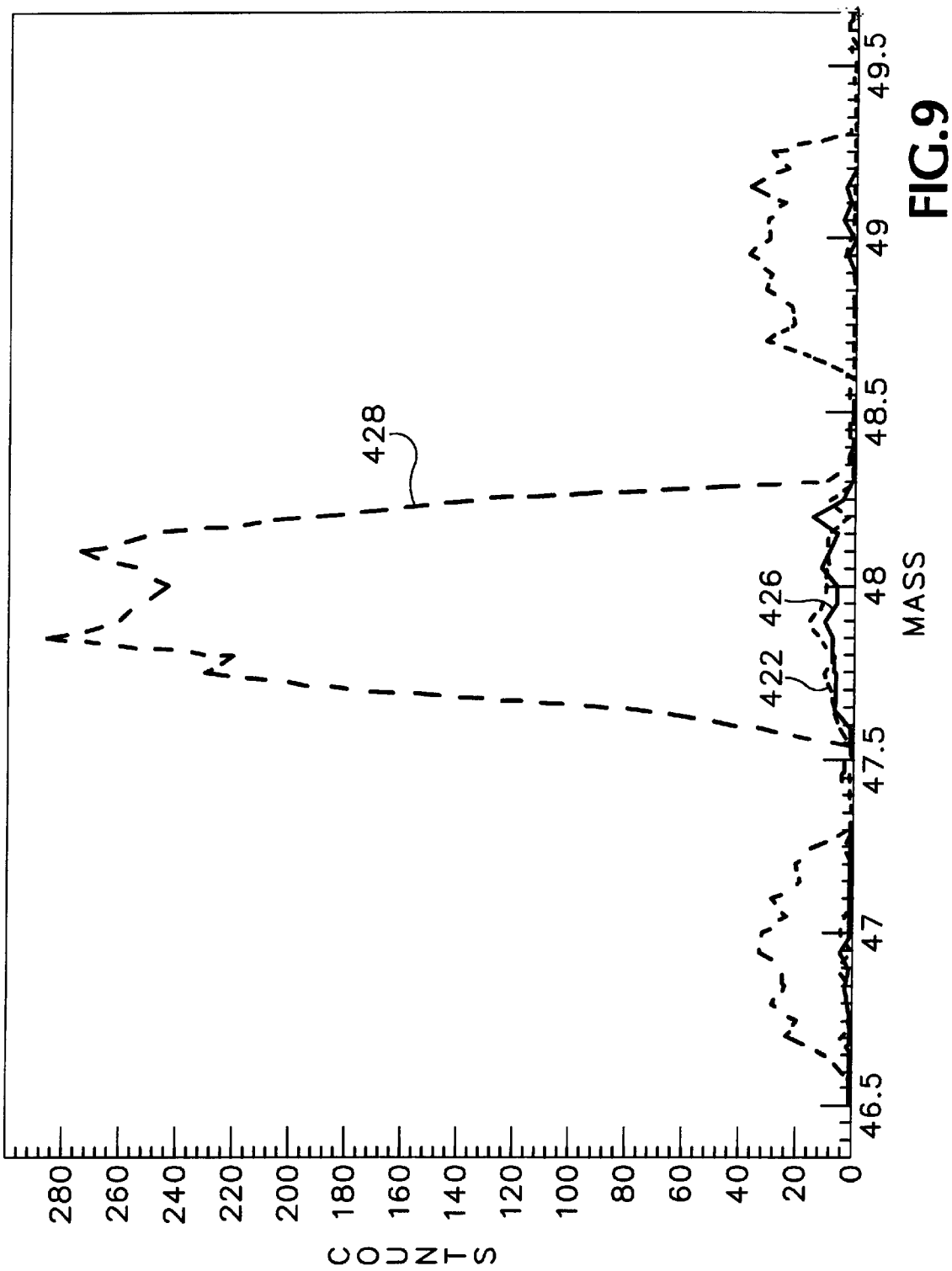
FIG. 9 shows a graph of the number of secondary ions detected from an titanium sample with and without using the present invention.

FIG. 9 is similar to FIG. 7 and 8, but the sample comprises primarily titanium. Line 422 shows the number of ions of different masses detected with no water vapor injection and with the gas injection needle 56 removed from the vicinity of the sample. Line 426 shows the number of ions of different masses detected with no water vapor injection, but with the gas injection needle 56 near the sample and electrically biased. The background vacuum pressure during ion counting for lines 422 and 426 was about $5.5 \times 10^{-7}$ mbar. Line 428 shows the number of ions of different masses detected with water vapor injection and with a bias voltage applied to the injection needle 56. The background vacuum pressure with water vapor injection present was about $3.3 \times 10^{-5}$ mbar. The total number of ions counted in the fixed time period with water vapor injection was 250, whereas the total number of ions counted without water vapor injection was 6 with the needle in and biased and 10 with the needle removed.

FIGS. 6, 7, and 8 show that the number of positive secondary ions detected increases greatly with the injection of water vapor. Water ($H_2O$) contains oxygen and is thought to effectively oxidize the sample surface. On certain materials, water enhances secondary ion yield more than does oxygen perhaps because water may stick to the surface more efficiently than oxygen, thereby increasing the probability of reaction with the ejected material. Other compounds, particularly oxygen bearing compounds such as $H_2O_2$, may also be useful for increasing the yield of secondary positive ions.

Water vapor introduction and ion bombardment do not need to be simultaneous. Significant enhancement is achieved by doing the SIMS analysis after depositing water and retracting the water source needle 56 out of the secondary ion extraction field.

The use of water vapor also increases ion yields of boron, carbon, sodium, potassium, calcium, nickel, iron, chromium, tantalum, copper, arsenic, molybdenum, tungsten, and phosphorus. Table 1 shows the factor by which ion yield increased for several materials tested.

TABLE 1

| Element | Yield Factor Increase |
| --- | --- |
| Silicon | 28 |
| Aluminum | 10 |
| Titanium | 25 |
| Molybdenum | 4 |
| Tungsten | 3 |

The invention is particularly useful for semiconductor defect analysis. It can be used to identify the elemental content of contaminant particles and other residues and impurities and defects, either on a surface or buried. Particles one half or one third the size of feature dimensions can destroy a circuit. With features on the order of 0.18 microns, particles as small as 0.06 microns can ruin an integrated circuit. The high precision of the liquid metal ion beam, combined with the enhanced ion yield of the present invention allows the element content of extremely small contaminants to be determined, so a process engineer can track down the source of the contamination and increase the process yield. The finely focused gallium beam can mill through processing layers to expose the circuit at the point of failure and then use SIMS to analyze the cause of the failure.

Gas injection systems are available on many existing LMIS FIB systems, so the invention allows the use of such systems without modification for sub-micron elemental SIMS analysis. For FIB systems lacking a gas injection system, one can be readily added. Of course, the invention is still applicable to FIBs using different ion sources, such as a duoplasmatron, and primary ions of other species, such as oxygen, argon, nitrogen, etc. Other types of mass analyzers, such as magnetic sector mass analyzers and a time-of-flight mass analyzers can also be used. Skilled persons will also understand that the invention is applicable to analytical systems that use other means, such as lasers or field ionization, to remove ionized particles for detection.

The embodiments described above are merely illustrative and skilled persons can make variations on them without departing from the scope of the invention, which is defined by the following claims.

What is claimed is:

1. A method of secondary ion mass spectrometry comprising:

positioning a sample to be analyzed within an enclosed chamber, supplying water vapor within said chamber, generating an ion beam, directing said ion beam toward said surface for sputtering secondary ions from at least a portion of said surface, receiving secondary ions from said surface of said sample, and directing said secondary ions to a mass analyzer.

2. The method according to claim 1 wherein directing said secondary ions to mass analyzer includes directing positive ions to the mass analyzer.

3. The method according to claim 1 wherein said water vapor is provided within said chamber by heating a hygroscopic material within said chamber.

4. The method according to claim 1 wherein said water vapor is provided from a reservoir outside said chamber.

5. The method according to claim 1 wherein supplying water vapor within said chamber includes directing water vapor through an injection needle toward said surface.

6. The method according to claim 5 wherein directing water vapor through an injection needle including electrically biasing the injection needle.

7. The method according to claim 6 wherein electrically biasing the injection needle including biasing the needle to optimize the secondary ion detection.

8. The method according to claim 1 wherein said ion beam is generated employing a liquid metal ion source.

9. The method according to claim 8 wherein said liquid metal comprises gallium.

10. The method according to claim 1 wherein directing said ion beam toward said surface includes directing the ion beam in a pattern to map materials present within a defined area, to determine a mass spectrum of the sample, or to determine a depth profile of materials present in the sample.

11. The method according to claim 1 including substantially evacuating said chamber for maintaining the interior of the chamber at a low pressure.

12. A method of analyzing a sample comprising:

positioning said sample on a stage within a substantially gas tight chamber of a focused ion beam system, directing water vapor or hydrogen peroxide towards a region of said sample where analysis is desired, for enabling reaction between the water vapor and the material from which said sample is formed, generating a focused ion beam and directing said ion beam toward said region of said sample for generating secondary ions, and analyzing said secondary ions to determine the elemental makeup of said region of said sample with a mass analyzer.

13. The method according to claim 12 including, prior to said analyzing step, the step of machining said sample by sputtering with said ion beam for removing material above a level where analysis is desired.

14. A method of increasing the secondary ion yield of sample materials bombarded by an ion beam, said method comprising the steps of:

directing an ion beam toward a location on a sample material, and directing water vapor or hydrogen peroxide at said location while said ion beam is incident thereon for enhancing secondary ion yield for elemental analysis with a mass analyzer.

15. The method according to claim 14 wherein the ion beam is a focused ion beam from a liquid metal ion source.

16. The method according to claim 14 further including analyzing the mass of particles sputtered by the ion beam.

17. The method according to claim 16 further including milling said sample material with said ion beam prior to said mass analysis for the purpose of exposing material to be analyzed at a desired depth of said sample.

18. Apparatus for performing secondary ion mass spectrometry with respect to a sample, said apparatus comprising:

an ion source for directing an ion beam toward a sample, a water vapor source for directing water vapor or hydrogen peroxide toward the sample at the impact area of the ion beam, a mass analyzer for analyzing secondary ions from the sample; and the apparatus configured to direct the ion beam toward the sample to which water vapored is adhered while collecting secondary positive ions for analysis in the mass analyzer.

19. The apparatus according to claim 18 wherein said mass analyzer means comprises a quadrupole mass analyzer, a magnetic sector mass analyzer, or a time-of-flight mass analyzer.

20. The apparatus according to claim 18 wherein said water vapor source includes an electrically biased needle.

21. The apparatus according to claim 18 wherein said water vapor source includes a reservoir containing a hygroscopic material.

* * * * *